(12) United States Patent
Kemper et al.

(10) Patent No.: US 12,705,794 B2
(45) Date of Patent: Aug. 11, 2026

(54) METHOD AND DEVICE FOR REPRODUCING POSITION AND ORIENTATION OF (LONG) BONE FRAGMENTS

(71) Applicant: Stryker European Operations Limited, Carrigtwohill (IE)

(72) Inventors: Jakob Kemper, Heemstede (NL); Lars Metz, Kiel (DE); Ulrich Hoffmann, Breisach (DE); Fabian Huegle, March (DE); Andreas Petersik, Heikendorf (DE); Heiko Gottschling, Munich (DE); Manuel Schroeder, Elingen (DE)

(73) Assignee: Stryker European Operations Limited, Carrigtwohill (IE)

( * ) Notice: Subject to any disclaimer, the term of this patent is extended or adjusted under 35 U.S.C. 154(b) by 279 days.

(21) Appl. No.: 18/568,087

(22) PCT Filed: Jun. 8, 2021

(86) PCT No.: PCT/IB2021/055019
§ 371 (c)(1),
(2) Date: Dec. 7, 2023

(87) PCT Pub. No.: WO2022/259017
PCT Pub. Date: Dec. 15, 2022

(65) Prior Publication Data
US 2024/0273760 A1 Aug. 15, 2024

(51) Int. Cl.
*G06T 7/73* (2017.01)
*A61B 34/10* (2016.01)
(Continued)

(52) U.S. Cl.
CPC .................. *G06T 7/74* (2017.01); *G06T 7/13* (2017.01); *G06T 7/149* (2017.01); *G06T 7/75* (2017.01);
(Continued)

(58) Field of Classification Search
CPC .... G06T 7/74; G06T 7/75; G06T 7/13; G06T 7/149; G06T 2207/10081;
(Continued)

(56) References Cited

U.S. PATENT DOCUMENTS

2007/0208234 A1* 9/2007 Bhandarkar ............ G16Z 99/00 600/300
2013/0314440 A1 11/2013 Simon et al.
(Continued)

FOREIGN PATENT DOCUMENTS

WO 2021/108270 A1 6/2021

OTHER PUBLICATIONS

International Search Report for Application No. PCT/IB2021/055019 mailed Apr. 25, 2022, pp. 1-6.
(Continued)

*Primary Examiner* — Stephen G Sherman
(74) *Attorney, Agent, or Firm* — Lerner David LLP

(57) ABSTRACT

Method and device for reproducing position and orientation of bone and long bone fragments, and in particular to a method and device for reproducing position and orientation of bone and long bone fragments allowing an improved re-positioning and re-orientation of bone and long bone fragments.

20 Claims, 7 Drawing Sheets

(51) Int. Cl.
*G06T 7/13* (2017.01)
*G06T 7/149* (2017.01)
*G16H 50/50* (2018.01)

(52) U.S. Cl.
CPC ..... *A61B 34/10* (2016.02); *G06T 2207/10081* (2013.01); *G06T 2207/30008* (2013.01); *G16H 50/50* (2018.01)

(58) Field of Classification Search
CPC ....... G06T 2207/30008; G06T 2210/41; G06T 7/0014; G06T 7/33; G06T 19/006; G06T 2207/10072; G06T 2207/10116; G06T 2207/10136; G06T 2219/004; A61B 34/10; A61B 2034/105; A61B 2034/256; A61B 2090/365; A61B 2090/3966; G16H 50/50; G16H 20/40; G16H 30/40; G16H 70/60
See application file for complete search history.

(56) References Cited

U.S. PATENT DOCUMENTS

2018/0325599 A1 11/2018 Seo
2021/0366118 A1* 11/2021 Campbell ............... G06T 19/20

OTHER PUBLICATIONS

Irwansyah, I. et al: "Study on Repositioning of Comminuted Fractured Bones for Computer-Aided Preoperative Planning", Biomedical and Bioinformatics Engineering, Nov. 12, 2017 (Nov. 12, 2017), pp. 30-34, XP058381678.

Jimenez-Delgado, J. J. et al: "Computer assisted preoperative planning of bone fracture reduction: Simulation techniques and new trends" , Medical Image Analysis, vol. 30, May 2016, pp. 30-45, XP029458416.

* cited by examiner

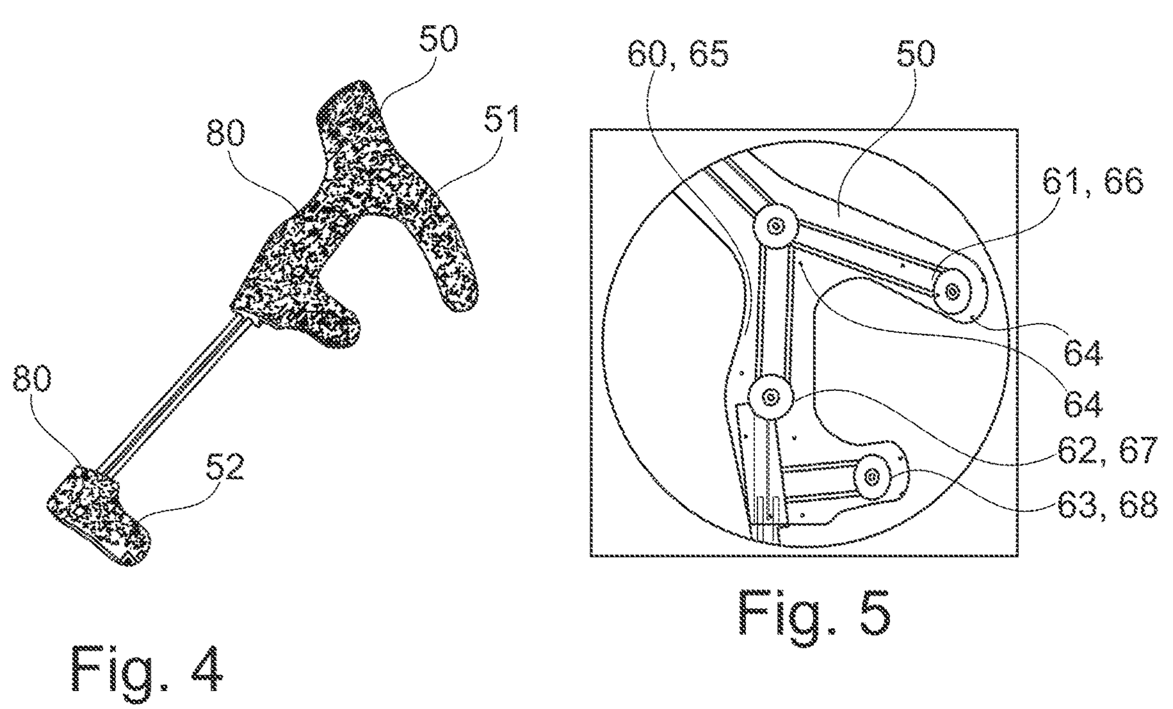
Fig. 4
Fig. 5
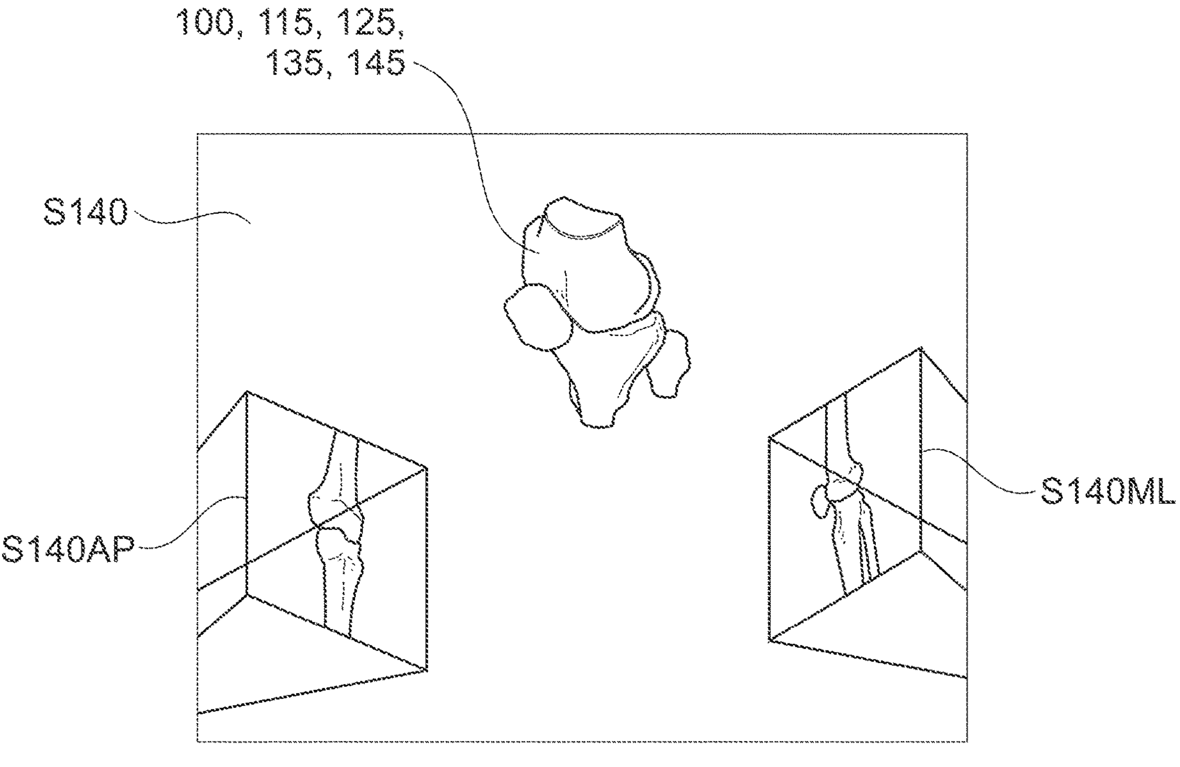
Fig. 6

METHOD AND DEVICE FOR REPRODUCING POSITION AND ORIENTATION OF (LONG) BONE FRAGMENTS

CROSS-REFERENCE TO RELATED APPLICATIONS

The present application is a national phase entry under 35 U.S.C. § 371 of International Application No. PCT/IB2021/055019, filed Jun. 8, 2021, published in English, the disclosures of which are incorporated herein by reference.

FIELD OF THE INVENTION

The present invention relates to a method and device for reproducing position and orientation of bone and long bone fragments, and in particular to a method and device for reproducing position and orientation of bone and long bone fragments allowing an improved re-positioning and re-orientation of bone and long bone fragments, and a corresponding computer program product and storage medium having stored thereon the computer program product.

BACKGROUND OF THE INVENTION

Surgical procedures have improved over the recent years. Significant improvements have been achieved by supporting systems for supporting the clinical personal in particular surgeons during surgeries. In particular bone fractures benefit from supporting systems for surgeons, which provide the surgeon with equipment, which allows the surgeon to improve exactness of repositioning of bone parts and positioning of implants, like screws, nails and bone plates, as well as tools and targeting and guiding devices.

As traumatized bones, i.e. fractures, have only a limited visual access, monitoring is usually based on radiating principles, like X-ray imaging or computer tomography CT images, or magnet resonance tomography MRT images. All these principles and methods involve at least one of the drawbacks of being radiation intensive, requiring large devices and requiring a considerable amount of time. Each monitoring step during a surgery prolongs the surgery duration and thus the duration of narcotic impact and increases costs and radiation impact. Nevertheless, when re-positioning and re-orientating bone fragments, a risk remains to not re-compose and re-construct the bone fragments as they have been before traumatization.

The primary target of orthopedic surgery on (long) bones after Trauma is to re-establish anatomical alignment to allow for return to full function as much as possible. Particularly in the lower extremity the goal is to (re-)establish a physiological gait. The surgeon tries to return the bone alignment to the pre-traumatic state. Practically always the exact pre-traumatic shape is unknown, so the comparison to an (unaffected) contra-lateral limb is a good available indicator of the patient's physiological anatomy. Best example here is the femoral shaft fracture. When reducing this fracture, the primary challenge is correctly dialing in the rotation of the Femur (also known as (Ante-)version or (Ante-)torsion). In some fractures pattern (e.g. oblique) the rotation can be re-established using simple alignment of the pieces, but in straight transverse or comminuted fracture patterns, the correct rotation has to be dialed in using other indicators. Currently some surgeons try to assess the resulting rotation of the bone intra-operatively, but reliability of these methods is low resulting in frequently in re-operations or gait issues for the patient resulting from a mal-rotated reduction.

Another common technique for Trauma surgeons is to try to determine version of the contra-lateral side in the beginning of the surgery and use this as a guidance. Determining the anteversion of a Femur without a CT is not trivial. Of both proximal and distal femur "perfect lateral" images have to be acquired and then the surgeon can for example compare the C-arm angles of these two images. Acquiring perfect laterals is very time and radiation consuming and with the current methods still quite in-accurate. This then also has to be done with the affected side which comes with similar challenges in acquiring these views correctly as on the unaffected limb. Furthermore, for assessing shortening and/or Varus/valgus there is currently no known method to properly compare to the contra-lateral limb outside of usage of complex Trauma navigation systems. Full length x-rays for the femur are currently unobtainable in the OR so connecting the proximal and distal portion of long bones is currently void of a practical solution. This is addressed in this invention.

Therefore, there is a need for surgery assisting methods and devices, which allow an increased the level of exactness of the re-composition of bone fragments.

SUMMARY OF THE INVENTION

The present invention provides a method and device for reproducing position and orientation of bone and long bone fragments, allowing an improved localization and positioning of bone fragments, and corresponding computer program products and storage mediums having stored therein the computer program product(s) according the subject matter of the independent claims. Further embodiments are incorporated into the dependent claims.

According to an aspect of the invention, there is provided a method for reproducing a position and orientation of bone fragments of a traumatized bone of an affected limb, the method comprises: imaging a plurality of bone fragments of a traumatized bone of an affected limb; identifying based on said imaging a contour, position and orientation of each of the plurality of the bone fragments of the traumatized bone of the affected limb; identifying based on at least one of the plurality of identified bone fragments a corresponding un-traumatized bone in a bone data base of three-dimensional bone models; allocating the plurality of identified bone fragments to corresponding contours and positions of the identified un-traumatized bone of the bone data base of three-dimensional bone models; visualizing the contour, position and orientation of each of the plurality of the bone fragments allocated to a corresponding contour, position and orientation of the identified un-traumatized bone of the bone data base of three-dimensional bone models, so that a re-composed position and orientation of each of the plurality of the bone fragments of the traumatized bone of the affected limb in a pre-traumatized state are recognizable.

Thus, a surgeon can be assisted in allocating bone fragments of rather complicated and multiple fractions to its original position and orientation. As the surgeon does have only limited optical access to the location of the fracture and it is often difficult for a surgeon to identify the fragments in a radio image, an ultrasound image or fluoroscope image, the method can assist the surgeon in identifying not only the bone fragments, but to also allocate the same to the original relative position and orientation with respect to each other. The bone data base provides the bone geometry of an unaffected bone or bone of an unaffected limb. The bone data base may be a collection of bone models. The bone models may be generated by a collection of 3-dimension bone geometry images, taken from real bones, a collection of 3-dimensional bone geometry reconstructions from 2-dimensional images of real bones, or from a bone model, which is represented by a modeling algorithm, which may generate a suitable bone model based on identifies contours of the fragments, and/or other relevant parameters from the individual patient. The data base may also include a bone models being generated from different of the above mentioned sources. Visual support as well as the comparison of anatomical measures like version/length/varus-angle etc. is possible.

According to an aspect of the invention, there is provided a method for reproducing a position and orientation of bone fragments of a traumatized bone of an affected limb, the method comprises: imaging a bone of an unaffected contra-lateral limb; identifying based on said imaging a contour, position and orientation of the bone of the unaffected contra-lateral limb; imaging a plurality of bone fragments of a traumatized bone of an affected limb; identifying based on said imaging of a plurality of bone fragments a contour, position and orientation of each of the plurality of the bone fragments of the traumatized bone of the affected limb; allocating the plurality of identified bone fragments to corresponding contours and positions of the identified contour, position and orientation of the bone of the unaffected contra-lateral limb; visualizing the contour, position and orientation of each of the plurality of the bone fragments allocated to a corresponding contour, position and orientation of the identified contour, position and orientation of the bone of the unaffected contra-lateral limb, so that a recomposed position and orientation of each of the plurality of the bone fragments of the bone of the affected limb in a pre-traumatized state are recognizable.

Thus, it is possible to use a contralateral bone for comparison, as it can be assumed that a contralateral bone has the same geometry as the traumatized or affected bone in its previous unaffected condition. The bone of the contralateral unaffected limb in its mirrored form can be used for allocation the bone fragments of the traumatized affected bone to the original position and orientation, so that in a recomposed state the affected bone corresponds to the mirrored unaffected bone. It should be noted that the steps as outlined above may at least in part be changed in sequence without departing from the purpose of the invention. For example imaging of an unaffected bone or a bone of an unaffected limb can be executed before imaging the affected bone or bone of the affected limb or after without departing from the purpose of the invention.

According to an embodiment the method further comprises confirming allocation by identifying based on at least one of the plurality of identified bone fragments a corresponding un-traumatized bone in a bone data base of three-dimensional bone models, and comparing the visualized contour, position and orientation of each of the plurality of the bone fragments allocated to a corresponding contour, position and orientation of the identified contour, position and orientation of the bone of the unaffected contra-lateral limb with the corresponding un-traumatized bone of the bone data base of three-dimensional bone models.

Thus, the basis for comparison can be double checked and confirmed. Identifying based on the contralateral limb may be executed before identifying based on a data base of bone models or after. It should be noted that in the same way comparison with a bone model from a bone model data base can be double checked by comparing the same with a comparison of a contra-lateral bone or limb.

According to an embodiment imaging a plurality of bone fragments of a bone of an affected limb is conducted as a three-dimensional imaging.

Thus, a more exact illustration and geometry may be identified at the affected bone and artefacts can be avoided, which may lead to misalignments. The three dimensional image may provide three dimensional contours of bone or bone fragments, which then can be used for comparison.

According to an embodiment imaging a plurality of bone fragments of a bone of an unaffected limb is conducted as a three-dimensional imaging.

Thus, a more exact illustration and geometry may be identified at the unaffected bone and artefacts can be avoided. The three dimensional image may provide three dimensional contours of bone or bone fragments, which then can be used for comparison.

According to an embodiment the three-dimensional imaging of a plurality of bone fragments of a bone of an affected limb is selected out of a group, the group consisting of computer tomographic scan, taking two or more three dimensional images and generating therefrom a three dimension image and ultrasonic imaging.

Thus, the surgeon may select an appropriate imaging method upon need and upon availability. Ultrasonic methods may provide lower radiation expositions, whereas x-ray based methods may provide more detailed structures. If sufficient details can be obtained by ultrasonic methods, the surgeon may select the same for reducing the radiation exposure.

According to an embodiment allocating the plurality of identified bone fragments to corresponding contours and positions of the identified bone of the bone data base of three-dimensional bone models, comprises a best fit contour algorithm with iterative closest point algorithm.

Thus, the allocation may be based on a variety of different points and contours and may compute the best fit. The algorithm may be applied repeatedly and iteratively until a sufficient match is achieved. It should be noted that the allocation and the application of the algorithm may take place alternated and repeatedly until a sufficient match is achieved, which is below a predetermined tolerance level.

According to an embodiment allocating the plurality of identified bone fragments to corresponding contours and positions of the identified bone of the bone data base of three-dimensional bone models comprises a best fit algorithm based on an identification of characteristic anatomical landmarks and/or characteristic axes and bring them into congruence.

Thus, the allocation may be based on a variety of characteristic landmarks and axes which can be easily identified and may compute the best fit. The algorithm may be applied repeatedly and iteratively until a sufficient match is achieved. It should be noted that the allocation and the application of the algorithm may take place alternated and repeatedly until a sufficient match is achieved, which is below a predetermined tolerance level.

According to an embodiment visualizing the contour, position and orientation of each of the plurality of the bone fragments allocated to a corresponding contour, position and orientation of the identified contour, position and orientation of the bone of the unaffected contra-lateral limb or the of the bone data base includes allocating each of the plurality of the bone fragments a different color.

Thus, the surgeon may easily identify the different matching contours and allocate the same to the reconstructed order. The color code may also include a sequence on how to reconstruct a plurality of fragments and may also include an identification of missing fragments, which could not be allocated, as they were hidden behind a larger fragment.

According to an embodiment the method further comprises visualizing a contour, position and orientation of each of the plurality of the identified bone fragments of the bone of the affected limb in their pre-re-composed state.

Thus, the surgeon may not only recognize the identified fragments, but may also be supported in relocating the fragments into the original position and orientation.

According to an embodiment visualizing a contour, position and orientation of each of the plurality of the identified bone fragments of the traumatized bone of the affected limb in their pre-re-composed state includes visualizing each of the plurality of the bone fragments in a different color corresponding to an allocated color of the plurality of re-composed bone fragments.

Thus, the surgeon may immediately recognize and identify, which fragment of the affected bone is to be positioned in the reconstructed bone.

According to an embodiment visualizing the identified contour, position and orientation of the bone fragments includes visualizing of characteristic landmarks and/or characteristic axes of the respective visualized bone fragments and bones.

Thus, the surgeon may double check, whether the recomposed bone matches a corresponding adjacent bone. This may be important for joints, e.g. the knee joint. The surgeon then may compare whether the axis of the affected but recomposed bone matches with the axis of the adjacent bone. The method may also compute a best match in case the reconstruction of the bone alone does not best fit to the axis of the adjacent bone.

According to an embodiment visualizing the identified contour, position and orientation of the plurality of bone fragments includes establishing a congruence of one of the bone fragments with a corresponding contour, position and orientation of the corresponding bone of at least one of the unaffected limb and the bone data base, and visualizing a spatial deviation of the incongruent other ones of the of the bone fragments.

Thus, the surgeon may recognize the deviation and may decide based thereon in how far and whether it is necessary to further correct and reconstruct the position and orientation of the fragments.

According to an embodiment the method further comprises determining an amount of spatial deviation of the visualized incongruent bone fragments from the corresponding contour, position and orientation of the corresponding of at least one of the unaffected limb and the bone data base.

Thus, the surgeon may receive a quantitative amount of the deviation which may help in deciding in how far correction of a position and orientation of bone fragments is necessary.

According to an embodiment the method further comprises outputting instructions to a user on how to change a position and orientation of the incongruent bone fragments so as to arrive at a more visualized congruence of the incongruent bone fragments with the corresponding bone of at least one of the unaffected limb and the bone data base.

Thus, the surgeon may receive detailed instructions by which amount the respective fragments are to be moved and also which fragment is to be replaced first.

According to an embodiment at least one of visualizing the contour, position and orientation of each of the plurality of the bone fragments allocated to a corresponding contour, position and orientation of the corresponding bone of at least one of the unaffected limb and the bone data base; determining an amount of spatial deviation of the visualized incongruent bone fragments from the corresponding contour, position and orientation of the corresponding bone of at least one of the unaffected limb and the bone data base; and outputting instructions to a user on how to change a position and orientation of the incongruent bone fragments so as to arrive at a more visualized congruence of the incongruent bone fragments with the corresponding bone of the unaffected limb or from the bone data base, respectively, is repeated until a predetermined amount of visualized congruence of the incongruent bone fragments with the corresponding bone of the unaffected limb or from the bone data base, respectively, is achieved.

Thus, an iterative process may be achieved which may lead to a better reconstruction result. The repetition may be reflected automatically, so that the repetition of respective steps takes place until a match within predetermined tolerance is achieved. The method may also include a decision algorithm which may selectively decide which step is to be repeated an in which sequence.

According to an embodiment there is provided a computer program product, which when carried out executes the method for reproducing a position and orientation of bone fragments as describe above.

According to an embodiment there is provided a data storage medium having stored thereon an executable code of the computer program product as described above.

According to an embodiment there is provided a device for carrying out a method for reproducing a position and orientation of bone fragments, wherein the device is adapted for carrying out the method as described above. The device may have an imaging interface for providing images and may have a user interface for interacting with a surgeon, which may include entering parameters, parameter selections or selection options suggested by the method, and outputting graphical presentations on a screen or a surgeon worn display device, like augmented reality glasses.

According to an aspect of the invention, there is provided a method for reproducing a position and orientation of long bone fragments of a long bone of an affected limb, the method comprises: imaging a long bone of an unaffected contra-lateral limb; identifying based thereon a contour, position and orientation of the long bone of the unaffected contra-lateral limb; imaging long bone fragments of a long bone of an affected limb; visualizing the identified contour, position and orientation of the long bone of the unaffected contra-lateral limb together with a visualization of long bone fragments of the long bone of an affected limb, so that deviations of positions and orientations of the long bone fragments are recognizable.

Thus, it is possible to use a contralateral bone for comparison, as it can be assumed that a contralateral bone has the same geometry as the traumatized or affected bone in its previous unaffected condition. The bone of the contralateral unaffected limb in its mirrored form can be used for allocation the bone fragments of the traumatized affected bone to the original position and orientation, so that in a recomposed state the affected bone corresponds to the mirrored unaffected bone. It should be noted that the steps as outlined above may at least in part be changed in sequence without departing from the purpose of the invention. For example imaging of an unaffected bone or a bone of an unaffected limb can be executed before imaging the affected bone or bone of the affected limb or after without departing from the purpose of the invention. Visual support as well as the comparison of anatomical measures like version/length/varus-angle etc. is possible.

According to an embodiment imaging a long bone of an unaffected contra-lateral limb comprises imaging a first end of the long bone of an unaffected contra-lateral limb and separately imaging a second end of the long bone of an unaffected contra-lateral limb.

Thus, the orientation of the unaffected bone or bone of the unaffected limb can be identified and the position and orientation of the affected bone or bone of the affected limb can be reconstructed. It should be noted that for this purpose it is not required taking an image of the entire long bone, but the imaging can be limited to the relevant portions of the long bone at the both ends, where the ling bone interfaces adjacent bones. This reduced radiation exposure significantly, in particular when taking three dimensional images.

According to an embodiment imaging a long bone of an unaffected contra-lateral limb comprises taking a first image from a first side of the long bone and taking a second image from a second side of the long bone being different from the first side.

Thus, when taking at least two two-dimensional images for reconstructing a three-dimensional image, the different viewing directions may serve for a reliable identification of the position and orientation, in particular rotational orientation with respect to the longitudinal axis of the long bone.

According to an embodiment taking the first image is from a first lateral side view onto the long bone and taking the second image is taken from a second lateral side view onto a long bone which is rotated over the first lateral side view by an angle of between 60° and 120°, in particular taking a first image is conducted from a medio-lateral ML direction and taking a second image is conducted from an anterior-posterior AP direction.

Thus, when taking at least two two-dimensional images for reconstructing a three-dimensional image, the large angle of different viewing directions may serve for a reliable identification of the position and orientation. ML and AP views may illustrate the most relevant views onto the anatomy and allow reconstruction of position and orientation, in particular rotational orientation with respect to the longitudinal axis of the long bone.

According to an embodiment imaging a long bone of an unaffected contra-lateral limb includes imaging a long bone of an unaffected contra-lateral limb having attached thereto a surgical reference body with a radio dense geometry having a unique radio projection for each orientation of the surgical reference body, and representing an unambiguous position and orientation of the long bone of the unaffected contra-lateral limb.

Thus, the reference body provides a reliable indicator for the spatial orientation of the view and the bone. The reference body may be composed of a plurality of radio dense or radio opaque fiducial markers being spatially arranged so as to provide a unique projection for each relevant viewing direction. This does not exclude that the reference body has same projections from different viewing directions, as long it is clear for the surgeon that these viewing directions can be distinguished for other reasons, e.g. because the other viewing directions are nonsense.

According to an embodiment imaging a first end and imaging a second end of a long bone of an unaffected contra-lateral limb includes imaging a first end of the long bone of an unaffected contra-lateral limb together with a first radio dense sub-geometry of the radio dense geometry of the surgical reference body and imaging a second end of the long bone of an unaffected contra-lateral limb together with a second radio dense sub-geometry of the radio dense geometry of the surgical reference body, wherein each of the first radio dense sub-geometry and the second radio dense sub-geometry has a unique radio projection for each orientation of the surgical reference body, allowing identification of a contour, position and orientation of a first end and a second end of the long bone of the unaffected limb separately and relative to each other.

Thus, each of the images can be identified with respect to its viewing direction, so that the orientation of the bone portion and the reference body's sub-geometry is reproducible. In case the two or more radio dense sub-geometries are positioned with respect to known position and orientation, the position and orientation of the bone parts can be determined based thereon.

According to an embodiment the reference body may have an optical pattern, which may allow optical identification or position and orientation of the reference body or parts thereof. The reference body may be separated in two or more parts, which can be reproducibly displaced with respect to each other, e.g. by a defined rotation, a defined displacement or a combination thereof.

Thus, if the measure of rotation and displacement is known, also the relative position and orientation of the radio dense sub-geometries can be determined and thus the position and orientation of the bone parts. Once the relative position of the radio dense sub-geometry with its unique radio projection with the respective bone part is established by fixing the respective part of the reference body to the respective part of the bone, the position and orientation can be monitored by the respective optical pattern which is adhered to the reference body, in particular to the respective displaceable and rotatable parts of the reference body.

According to an embodiment identifying a contour, position and orientation of the long bone of the unaffected contra-lateral limb comprises identifying a corresponding long bone in a bone data base of three-dimensional long-bone models including at least one of a contour, a position and an orientation of a corresponding long bone.

Thus, a surgeon can be assisted in recomposing the original position and orientation of the long bone portions. The bone data base may assist the surgeon in allocating the bone portions the original relative position and orientation with respect to each other. The bone data base provides the bone geometry of an unaffected bone or bone of an unaffected limb. The bone data base may be a collection of bone models. The bone models may be generated by a collection of 3-dimension bone geometry images, taken from real bones, a collection of 3-dimensional bone geometry reconstructions from 2-dimensional images of real bones, or from a bone model, which is represented by a modeling algorithm, which may generate a suitable bone model based on identifies contours of the fragments, and/or other relevant parameters from the individual patient. The data base may also include a bone models being generated from different of the above mentioned sources.

According to an embodiment imaging long bone fragments of a long bone of an affected limb comprises imaging a first fragment of the long bone of an affected limb corresponding to a first end of the long bone of a contra-lateral unaffected limb and separately imaging a second fragment of the long bone of an affected limb corresponding to a second end of a long bone of a contra-lateral unaffected limb.

Thus, the orientation of the unaffected bone or bone of the unaffected limb can be identified and the position and orientation of the affected bone or bone of the affected limb can be reconstructed. By limiting imaging to the relevant portions of the long bone at the both ends, radiation exposure is reduced significantly, in particular when taking three dimensional images.

According to an embodiment the method further comprises identifying a contour, position and orientation of the long bone fragments of the affected limb and identifying based thereon long bone fragments in a bone data base of three-dimensional long bone models including a contour, position and orientation of a corresponding long bone.

Thus, a surgeon can be assisted in recomposing the original position and orientation of the long bone portions. The bone data base provides the bone geometry of an affected bone or bone of an affected limb.

According to an embodiment visualizing the identified contour, position and orientation of the long bone of the unaffected contra-lateral limb together with a visualization of long bone fragments of a long bone of an affected limb includes visualizing of at least one of characteristic landmarks and characteristic axes of the respective visualized long bones.

Thus, the surgeon may receive additional support for identifying the required reconstructed position and orientation of the bone parts or fragments. The allocation then may be based on a variety of characteristic landmarks and axes which can be easily identified. The surgeon may double check, whether the recomposed bone matches a corresponding adjacent bone. This may be important for joints, e.g. the knee joint. The surgeon then may compare whether the axis of the affected but recomposed bone matches with the axis of the adjacent bone.

According to an embodiment visualizing the identified contour, position and orientation of the long bone of the unaffected contra-lateral limb together with an visualization of long bone fragments of a long bone of an affected limb includes establishing a congruence of one of the first long bone fragment and the second long bone fragment of the long bone of the affected limb with the corresponding one of the first end and second end of the long bone of the unaffected limb, and visualizing a deviation of the incongruent other one of the first fragment and the second fragment of the long bone of the affected limb from the corresponding end of the long bone of the unaffected limb.

Thus, the surgeon may recognize the deviation and may decide based thereon in how far and whether it is necessary to further correct and reconstruct the position and orientation of the first and second long bone fragments in order to achieve a congruence between the affected bone with the unaffected bone.

According to an embodiment visualizing the identified contour, position and orientation of the long bone of the unaffected contra-lateral limb together with an visualization of long bone fragments of a long bone of an affected limb includes establishing a congruence of one of the first long bone fragment and the second long bone fragment of the long bone of the affected limb with the corresponding one of a first end and second end of a long bone of a data base of three-dimensional bone models, and visualizing a deviation of the incongruent other one of the first fragment and the second fragment of the long bone of the affected limb from the corresponding end of the long bone of the data base of three-dimensional bone models.

Thus, the surgeon may recognize the deviation and may decide based thereon in how far and whether it is necessary to further correct and reconstruct the position and orientation of the first and second long bone fragments in order to achieve a congruence between the affected bone with the identified bone from the bone data base.

According to an embodiment the method further comprises determining an amount of spatial deviation of the visualized incongruent other one of the first fragment and the second fragment of the long bone of the affected limb from the corresponding end of the long bone of the unaffected limb.

Thus, the surgeon may receive a quantitative amount of the deviation which may help in deciding in how far correction of a position and orientation of long bone fragments is required.

According to an embodiment the method further comprises outputting instructions to a user on how to change a position and orientation of the incongruent other one of the bone fragment and the second fragment of the ling bone of the affected limb so as to arrive at a more visualized congruence to the corresponding end of the long bone of the unaffected limb.

Thus, the surgeon may receive detailed instructions by which amount the respective long bone portions or fragment are to be moved and into which direction.

According to an embodiment at least one of visualizing the identified contour, position and orientation of the long bone of the unaffected contra-lateral limb together with an imaging of bone long bone fragments of a long bone of an affected limb; determining an amount of spatial deviation of the visualized incongruent other one of the first fragment and the second fragment of the long bone affected limb from the corresponding end of the long bone of the unaffected limb; and outputting instructions to a user on how to change a position and orientation of the incongruent other one of the first fragment and the second fragment of the affected limb so as to arrive at more visualized congruence to the corresponding end of the long bone of the unaffected limb is repeated until a predetermined amount of visualized congruence of the other one of the first fragment and the second fragment of the long bone of the affected limb and the corresponding end of the long bone of the unaffected limb is achieved.

Thus, an iterative process may be achieved which may lead to a better reconstruction result. The repetition may be reflected automatically, so that the repetition of respective steps takes place until a match within predetermined tolerance is achieved. The method may also include a decision algorithm which may selectively decide which step is to be repeated an in which sequence.

According to an embodiment there is provided a computer program product, which when carried out executes the method reproducing a position and orientation of long bone fragments of a long bone of an affected limb as describe above.

According to an embodiment there is provided a data storage medium having stored thereon an executable code of the computer program product as described above.

According to an embodiment there is provided a device for carrying out a method reproducing a position and orientation of long bone fragments of a long bone of an affected limb, wherein the device is adapted for carrying out the method as described above. The device may have an imaging interface for providing images and may have a user interface for interacting with a surgeon, which may include entering parameters, parameter selections or selection options suggested by the method, and outputting graphical presentations on a screen or a surgeon worn display device, like augmented reality glasses.

BRIEF DESCRIPTION OF THE FIGURES

The invention will be described by way of the following drawings, which illustrate in FIG. 1: illustrates segmented CT scan of a fracture in original (displaced) state according to an exemplary embodiment.

FIG. 4: illustrates an exemplary embodiment of a reference body (radiolucent) in a perspective view with radio dense marking patterns.

FIG. 5: illustrates an exemplary embodiment of a reference body in x-ray view with reference pattern(s).

FIG. 6: illustrates a 2D to 3D visualization according to an exemplary embodiment.

It should be noted that same or similar reference numerals illustrate same or similar components. Along these Figures exemplary embodiments of the invention will be described as follows.

DETAILED DESCRIPTION OF EXEMPLARY EMBODIMENTS

Figures 1, 2, 3:
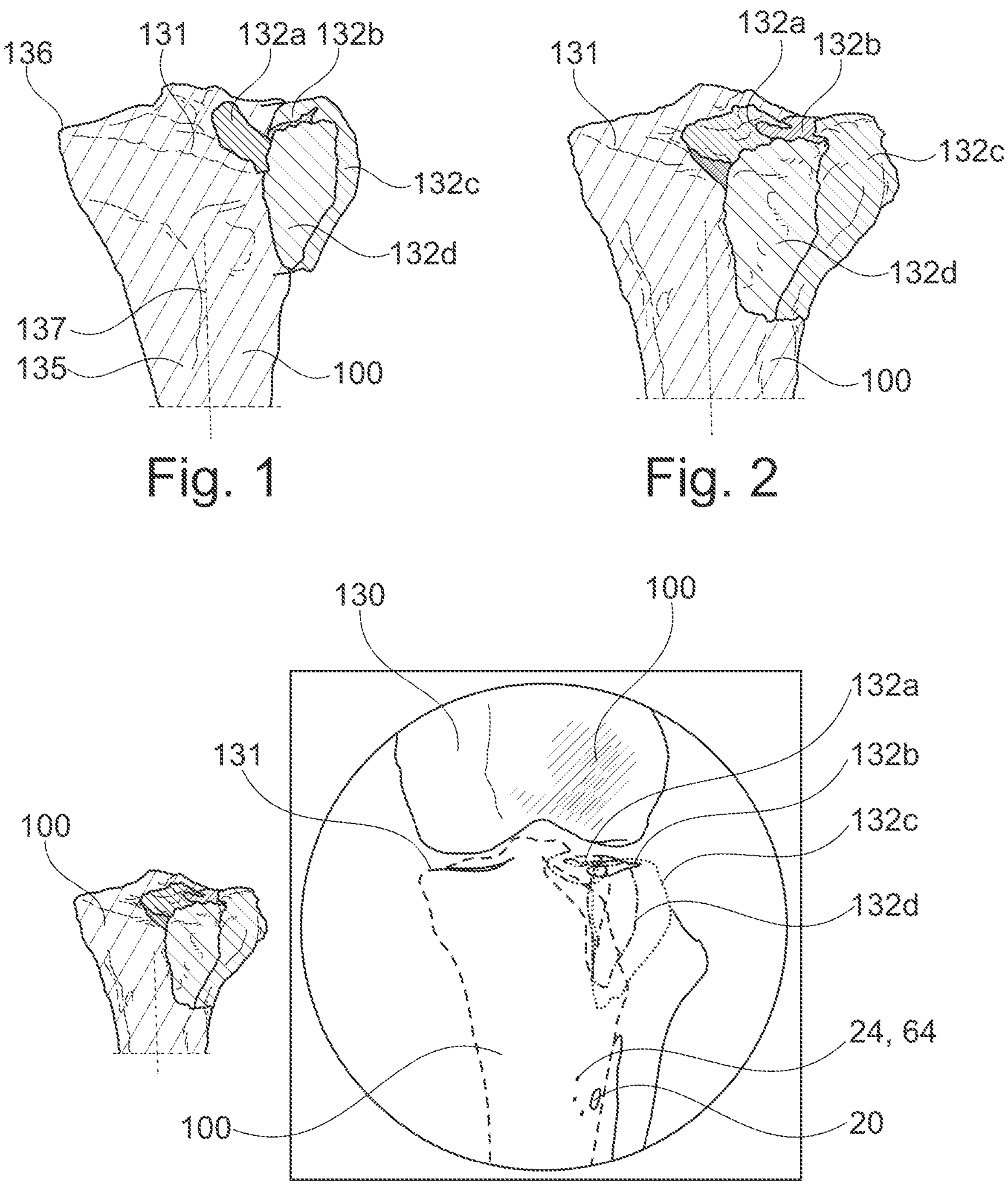
FIG. 2: illustrates segmented CT scan of a fracture in a virtually reduced (corrected) state according to an exemplary embodiment.
FIG. 3: illustrates an overlay of a virtually reduced target contour in intra-operative fluoroscope according to an exemplary embodiment.

FIG. 1 illustrates segmented CT scan of a fracture in original (displaced) state according to an exemplary embodiment. The patient's anatomy 100 in form of a traumatized bone 135 has several fragments 131, 132*a-d*. Here a large fragment 130 serves as a basis for the application of the method for reconstructing a bone structure. The traumatized bone 135 has a characteristic axis 137. The bone fragments, in particular here the large bone fragment 131 can be identified by the axis 137 and a characteristic landmark 137. These both characteristic items allow an identification of a respective bone in a bone data base, which then may serve as a reference for reconstruction. The smaller bone fragments 132*a*, 132*b*, 133*c*, 132*d* in FIG. 1 are already identified and allocated to a particular color (illustrated by different filling patterns in the Figures).

FIG. 2 illustrates segmented CT scan of a fracture in a virtually reduced (corrected) state according to an exemplary embodiment. The bone fragments 132*a*, 132*b*, 133*c*, 132*d* from FIG. 1 are brought into the corrected reduced, i.e. reconstructed position and orientation with respect to the reference fragment 131, so that the patient's anatomy in form of a traumatized bone 135 is reconstructed.

FIG. 3 illustrates an overlay of a virtually reduced target contour in an intra-operative fluoroscope/radio image, aided by reference body 20. The fiducial markers 24, 64 are visible as dots on the tibia, which is the larger one of the bottom bones. The bone fragments 132*a*, 132*b*, 133*c*, 132*d* of FIG. 1 and FIG. 2 are identified by identifying the respective contours and structures in the radio image, her a fluoroscope. Thus, the surgeon may recognize the different bone fragments 132*a*, 132*b*, 133*c*, 132*d*. The bone fragments after identification can be allocated to a particular color so that the different contours can be distinguished by the surgeon, even if not all edges an contours are visible in the 2-dimensional image.

FIG. 4 illustrates a reference body 50 (radiolucent) with radio dense marking patterns (not illustrated here). The here shown example for the femur is length adjustable, so that a first leg 51 may be displaced and/or rotated over a second leg 52 of the reference body. An optical pattern 80 as reference for Pattern Recognition Optics (PRO) technology can be incorporated on both legs 51, 52. Reference body here referring to structure that can be identified in the radiographic imaging with the purpose of identifying viewing direction and relate various images to each other. To account for different bone-length the reference body can be extendable, as it is illustrated in FIG. 4 or modular, for example with different lengths of distal components. For establishing a uniquely identifiable references in the x-rays, radio dense sub-geometries with a unique radio/x-ray projection are used, e.g. a irregular pattern of steel balls in a polymer-body. The patterns of steel marks are also denoted as fiducial markers and are designed to be uniquely identifiable from any viewing direction. However, any shapes visible in x-ray could be chosen to give the software the ability to know the relative projection angles and positions. It should be noted that the relative position of the both parts of the reference body as illustrated in FIG. 4 may be determined by connecting an optical imaging device to one of the parts of the surgical reference body. If the optical pattern of the other of the parts of the surgical reference body is known, and also the relative position and orientation of the pattern with respect to the connected part of the surgical reference body is known, with an also known position and orientation of the optical imaging device with respect to the one part of the surgical reference body, the relative position of an optical imaging device and an optical pattern, and thus of the both parts of the surgical reference body can be determined. If the optical pattern is known with respect to its structure and size, an image thereof allows to determine from where the image was taken. It is not required to take an image of the entire pattern, as long as the imaged portion of the pattern is unique in the entire pattern. Both, the optical imaging device and the optical pattern represent either a first part of a surgical reference body or second part of a surgical reference body. It is also possible that the entire surgical tracking system supports more than one optical imaging device and it also possible to support more than one optical pattern, so as to determine the relative spatial position and orientation of more than two parts of a surgical reference body. The optical pattern may be printed onto a respective part of the surgical reference body. If printed onto, embedded in or fixed to a part of the surgical reference body, the pattern makes the part of the surgical reference body to a reference body, as the pattern allows an optical referencing. For optical determination of a relative position and orientation, it is required that the relative position and relative imaging or viewing direction of the optical imaging device with respect to the part of the surgical reference body is known which is represented by the optical imaging device. Likewise, it is required that the optical pattern as such is known, as well as its relative position and relative orientation with respect to the part of the surgical reference body is known, which is represented by the optical pattern. If the relative position and orientation of the optical imaging device and the optical pattern with respect to each other can be determined, and the relative position and orientation of the each of the optical imaging device and the optical pattern with respect to the respective part of the surgical reference body is known which is represented by them, then it is possible to determine the relative position and orientation of the parts of the surgical reference body with respect to each other. This may be applied to extractable surgical reference bodies, which have at least two parts, one of which is provided with the optical pattern and the other of which is provided with the optical imaging device. The two or more parts of the surgical reference body may be used to be adapted to patient's anatomies which are very large and cannot be imaged by a single radio image. The parts, each of which may have a radio dense geometry or sub-geometry each having a unique projection in a radio image, may be illustrated in separate radio images. The spatial position and orientation can be carried out with the optical imaging device coupled to one part of the reference body and an optical pattern coupled to the other part of the surgical reference body, so that with the optical determination of the relative spatial position, also the spatial position of the radio dense (sub) geometries can be determined, including the bone parts of e.g. long bones, which are referenced with the parts of the surgical reference body. The parts of the surgical reference body may coupled to each other by a mechanical structure which selectively allows fixing and releasing of the parts of the surgical reference body with respect to each other. This can be done via a rail or a hinge, each having only one degree of freedom, or by a combination of one or more rail and one or more hinges allowing more than one degree of freedom. It should be noted that what is described in the following for a surgical instrument and a reference body also applies for a first part of a surgical reference body and a second part of a surgical reference body.

Figure 7:
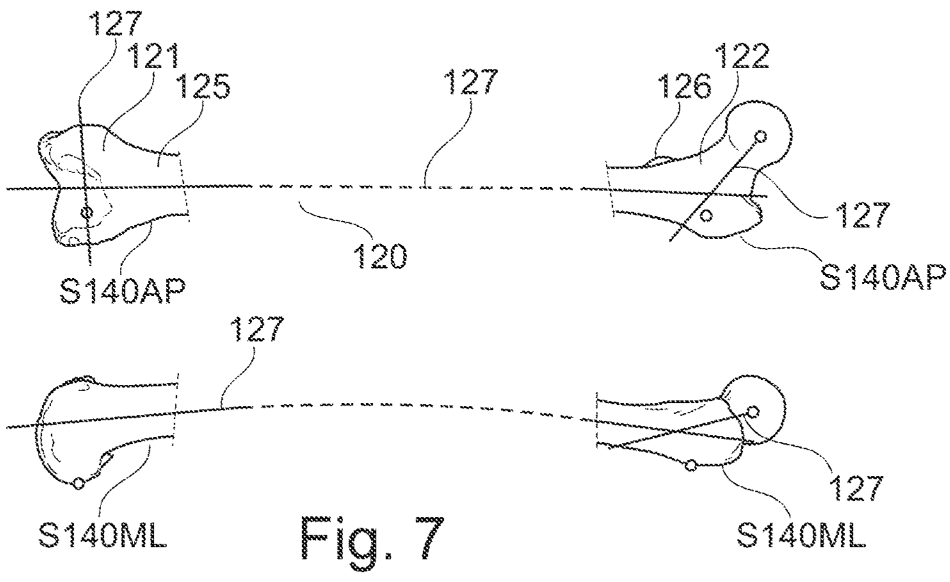
FIG. 7: illustrates 3D reconstruction of a long bone according to an exemplary embodiment.

These reference bodies enable relate multiple views of one anatomic region to each other which in turn allows a 3D-reconstruction of spatial relationships of anatomical landmarks and/or structures, for the femur e.g. the femoral head, femoral neck, proximal femoral shaft axis, condyles, distal joint axis etc. This can be done manually by asking the user to select bony landmarks and/or boundaries, such as femoral head outline, shaft, trochanters, condyles etc. on the screen. This information can be processed into a 3D approximation of the bone shape, e.g. by matching these landmarks to a statistical bone shape model from a bone database tools. This can be done automatically by usage of machine learning networks utilizing again bone database data. Reference bodies also enable relate images to bring anatomic landmarks in relation to each other of regions that cannot be covered in a single or even overlapping c-arm views. With this it is possible to establish relationships of proximal and distal bone portions and generate information like bone length, anteversion, arus/valgus etc. The combination of relate multiple views of one anatomic region and relate images to bring anatomic landmarks in relation to each other allows establishing a 3D model of a full long bone as shown in FIG. 7. An important aspect is to determine the spatial relationship of the two peri-articular areas (proximal and distal). It is not important in this case to reconstruct the center region of the bone, as the spatial position of the proximal and distal portion of the bone is given through the bone-spanning external reference body. Once 3D-models of the relevant portions are created, it is possible to identify all typical anatomic landmarks and axis automatically, in particular through active shape models. Anatomical axis like proximal and distal shaft axis, neck axis, center of femoral head etc. can be included in the 3D model.

The attachment/fixation of the reference body to the patient can be achieved in various ways. One way is to use skin stickers to attach the device to the patient, which e.g. can be connected with the push-button mechanism to the device and with a sticky side to the patient. As an alternative Velcro-straps or the like around the limb or (polyaxial) half-pins connecting the reference body directly and rigidly to the patient's bone can be used. It should be noted that the reference body could in large parts be replaced by using a robotic c-arm or other means of externally tracking the position of the C-arm relative to the patient. When having fixed the reference body to a patient's anatomy, both ends of a bone are referenced by a respective radio dense sub-geometry having a unique radio projection. If the measure of rotation and displacement is known, also the relative position and orientation of the radio dense sub-geometries can be determined and thus the position and orientation of the bone parts. Once the relative position of the radio dense sub-geometry with its unique radio projection with the respective bone part is established by fixing the respective part of the reference body to the respective part of the bone, the position and orientation can be monitored by the respective optical pattern 80 which is adhered to the reference body, in particular to the respective displaceable and rotatable parts of the reference body.

Medio-lateral ML direction is to be understood as a direction from the side to center or from the center to the side. Anterior-posterior AP direction is to be understood as a direction from the front side to the back side or from the back side to the front side.

FIG. 5 illustrates the reference body in x-ray view where the reference pattern can be seen. The corporal contour of the reference body 50 can be recognized as a light, but not very contrasted contour. Therefore, the reference body 50 includes a radio dense geometry 60, which has a unique radio projection 65. A radio projection is considered as projected image of a geometry onto a two-dimensional array. The radio dense geometry 60 may have a number of radio dense sub-geometries 61, 62, 63, each on which may have a unique radio projection 66, 67, 68, so that determination of a spatial position and orientation is possible with only one of the radio dense sub-geometries. The radio dense (sub-) geometry(ies) 60, 61, 62, 63 may have a number of fiducial markers 64, as described above with respect to FIG. 4.

FIG. 6 illustrates a 2D to 3D visualization. A 3D approximation is generated based on two or more 2D fluro/radio images with known relative positions of images, typically through a reference body in image, which is not shown here. The 3D approximation is executed based on imaging a bone S140. One image is taken from the medio-lateral ML direction S140ML and a further image is taken from the anterior-posterior direction S140AP. It should be noted that approximation is not limited to ML and AP view, but may also be carried out with two or more views different from ML and AP view. However, ML views and AP views are established in the art. From the ML and AP view a 3D reconstruction of the anatomy/bone can be carried out. This can be carried out for imaging an affected bone and an unaffected bone.

FIG. 7 illustrates 3D reconstruction of a long bone according to an exemplary embodiment. The long bone 125, here an unaffected long bone 125 is imaged only at its distal end 121 (here left) and its proximal end 122 (here right). The middle section is not imaged, as the middle section as such is not relevant for a reconstruction, as for the reconstruction only the relative position and orientation of the both distal and proximal end portion is relevant. For the orientation characteristic axes 127 and characteristic landmarks 126 of the long bone 125 are used. It should be noted that the characteristic axes 127, in particular the characteristic longitudinal axis 127 may be curved or composed of linear segments, as illustrated in FIG. 7 for the ML (bottom) view. The same applies mutatis mutandis also for an affected bone (not illustrated here). For further details, it is also referred to FIG. 11. Positioning of bone fragments, in particular bone fragments of long bone can be supported by intramedullary nails. For this purpose, an intramedullary nail can be introduced into the intramedullary canal so as to stabilize the relative position of the bone fragments, in particular a proximal fragment and a distal fragment with respect to its rotational position and longitudinal position. An intramedullary nail may be introduced before re-positioning based on the comparison between an affected bone and an unaffected bone, but may also be introduced after re-positioning for stabilizing purposes.

Figure 8:
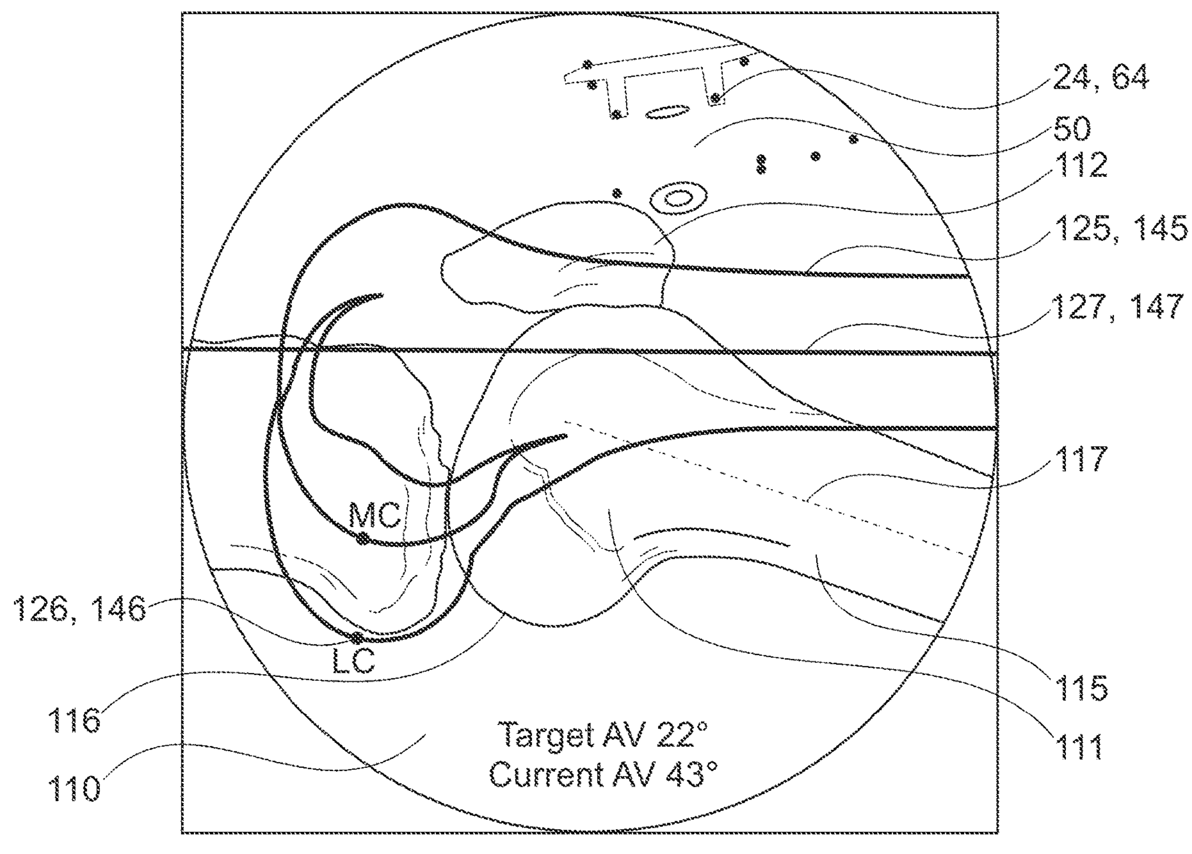
FIG. 8: illustrates a reduction assistance by image overlay of contra-lateral outlines according to an exemplary embodiment.

FIG. 8 illustrates a reduction assistance by image overlay of contra-lateral outlines according to an exemplary embodiment. The fluoroscope/radio image shows a limb 110 with the traumatized bone 115 with two fragments 111, 112, and with its characteristic axis 117 and a characteristic landmark 116. The position and orientation can be determined by a reference body 50 and its fiducial markers 24, 64. The radio image has augmented a contour of an unaffected bone 125, 145 with its characteristic axis 127, 147 and characteristic landmark 126, 146. The surgeon may align the augmentation to the main fragment 111 of the traumatize bone 115 and then further align the further fragments 112 to the main fragment 111 in order to arrive at the augmented contour 125, 145 of the unaffected bone.

Figure 9:
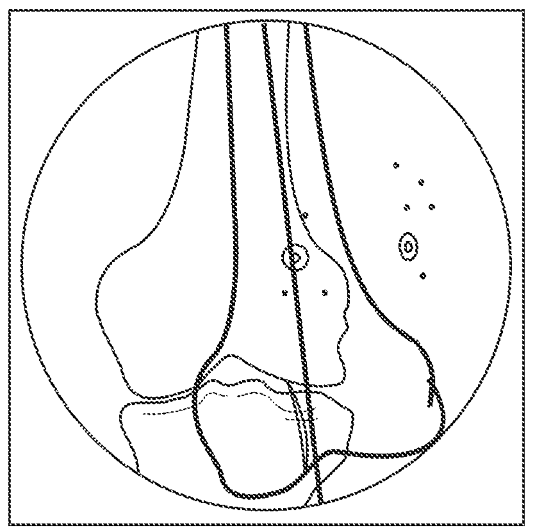
FIG. 9: illustrates a reduction assistance by image overlay of contra-lateral outlines in two different views according to an exemplary embodiment.
Figure 9:
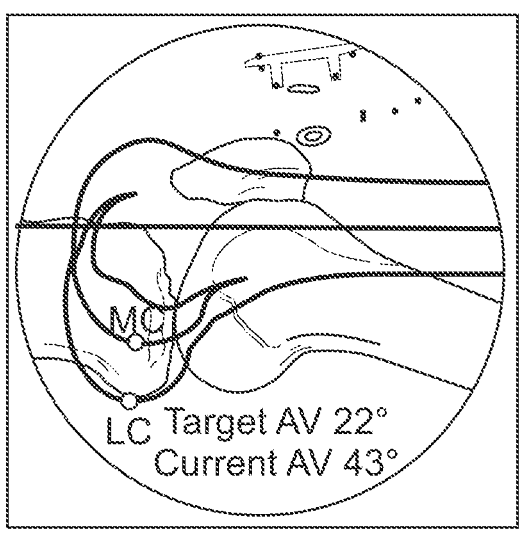

FIG. 9 illustrates a reduction assistance by image overlay of contra-lateral outlines in two different views according to an exemplary embodiment. The right view corresponds to the view of FIG. 8. Both views allow in identification of the position and orientation through the unique projection of the radio dense geometry of the reference body, as described with respect to FIG. 8.

Figure 10:
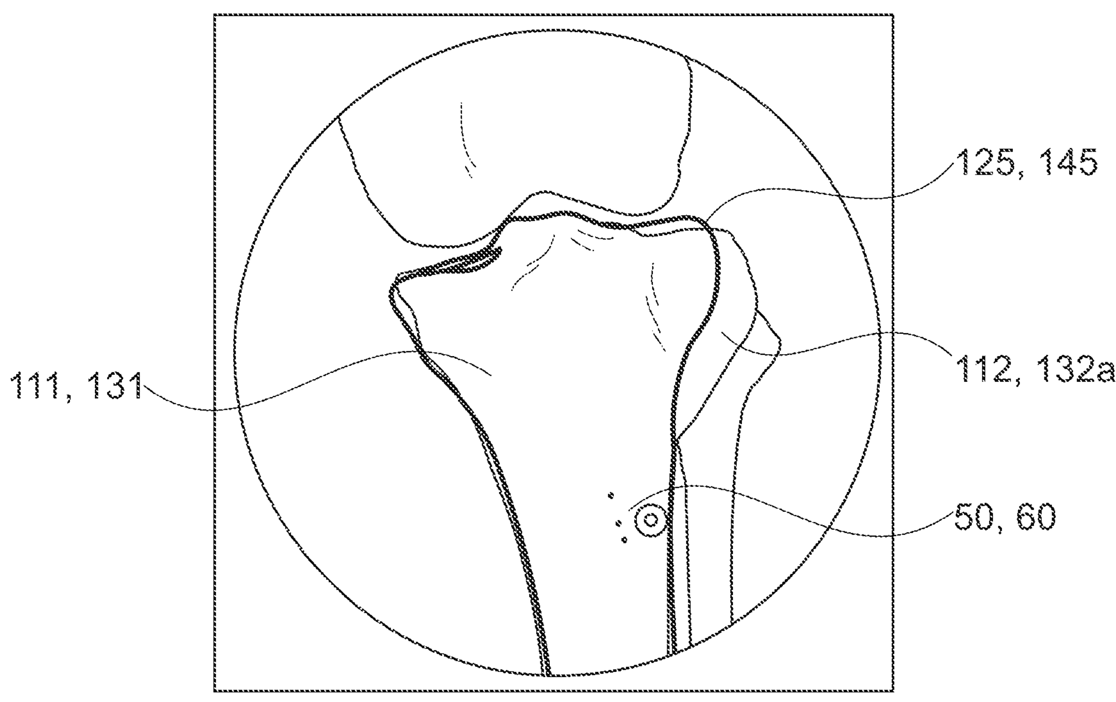
FIG. 10: illustrates a contour overlay of mirrored contralateral contour for intra-articular reduction support according to an exemplary embodiment.

FIG. 10 illustrates a contour overlay of mirrored contralateral contour of an unaffected bone 125, 145 for intra-articular reduction support according to an exemplary embodiment. As can be seen, the main fragment 111, 131 corresponds to the contour of the augmented contralateral bone 125, 145. It should be noted that the augmented contour may also be derived from a bone data base for the same purpose. The further fragment 112, 132*a* or any additional (here not illustrated) fragment 132*b*, 132*c*, 132*d* is not yet re-positioned in FIG. 10, but the surgeon may clearly recognize where the further fragment 112, 132*a* is to be positioned and oriented for meeting the contour of the unaffected bone 125, 145 or a corresponding contour from a bone data base.

Figure 11:
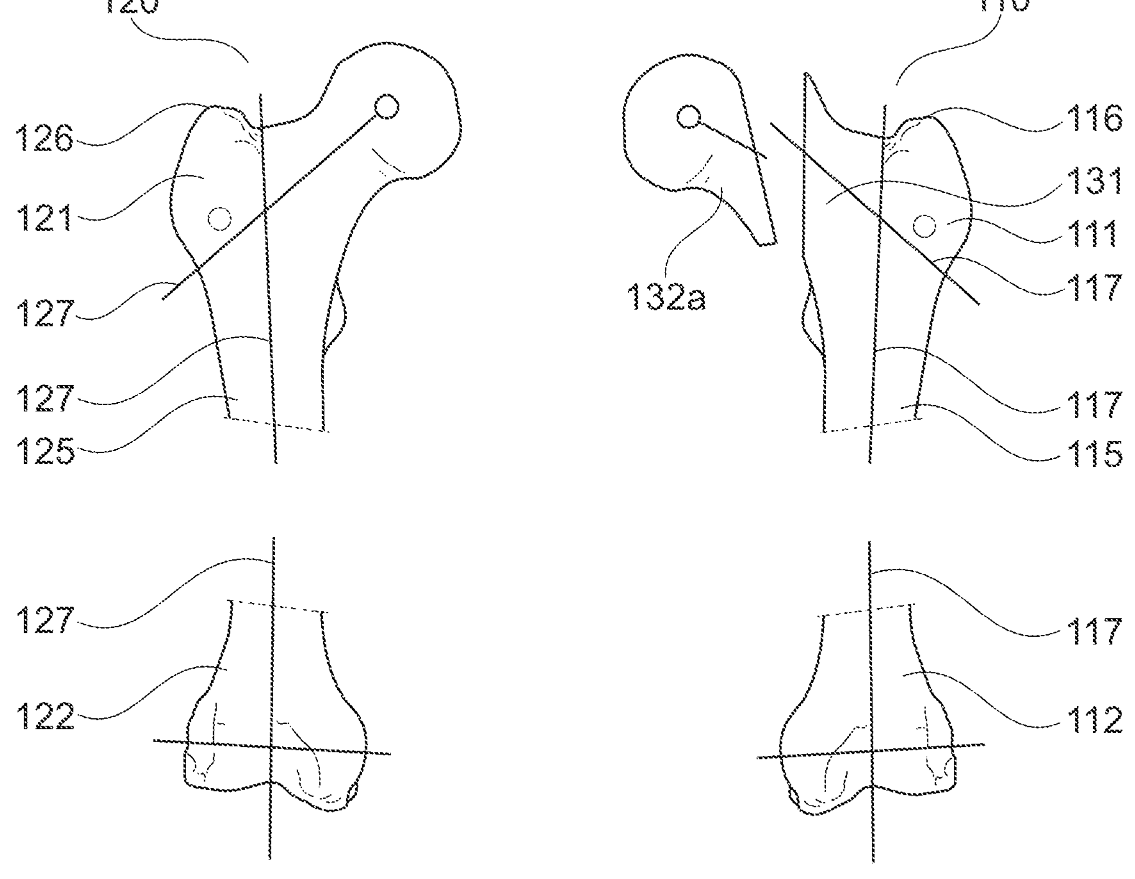
FIG. 11: illustrates vis a vis an unaffected bone (left) and an affected bone (right)

FIG. 11 illustrates vis a vis an unaffected bone (left) and an affected bone (right). An unaffected long bone 125 of an unaffected limb 120 is imaged only at its distal end 121 and its proximal end 122. The middle section is not imaged, as the middle section as such is not relevant for a reconstruction, as for the reconstruction only the relative position and orientation of the both distal and proximal end portion is relevant. For the orientation characteristic axes 127 and characteristic landmarks 126 of the long bone 125 are used. Likewise an affected long bone 115 of an affected limb 110 is imaged only at its distal end 111 and its proximal end 112. The middle section is not imaged, as the middle section as such is not relevant for a reconstruction, as for the reconstruction only the relative position and orientation of the both distal and proximal end portion is relevant. For the orientation characteristic axes 117 and characteristic landmarks 116 of the affected long bone 115, in particular its main fragment are used. Now the surgeon may reposition the further fragment 132*a* with respect to the main fragment 131 by comparing the affected bone 115 with the unaffected bone 125. The contour of the unaffected bone 125 then is mirrored and augmented to the affected bone, as it is illustrated in and describer with respect to FIG. 8 and FIG. 10.

Likewise a repositioning of the entire proximal end 111 (top) of an affected bone 115 over its distal end (112 (bottom) may be carried out, it the fracture line is somewhere in the middle portion of the affected bone 115, which is not imaged here. The procedure is the same as illustrated in and describer with respect to FIG. 8.

The procedure for such a long bone reduction assistance in length and rotation alignment will be described in general as follows. For this purpose, reference bodies combined with 2D to 3D reconstruction will be used, on the example of a femur reduction support by a suggested surgical sequence. First a 3D model as described with respect to FIG. 6 and FIG. 7 is generated of the unaffected (contra-lateral) bone/limb. For this, a reference body 50 spanning the length of the bone 125 of interest is placed on the unaffected limb 120. At least two images of the proximal area of the bone are taken (for ideal results the angle should be close to 90 degrees, in particular AP and ML, as describe with respect to FIG. 6. At least two images of the distal portion 122 of the bone are taken. Both groups of images are processed into a 3D approximation of the bone (2D to 3D or manual method) and landmarks 126 and axis/axes 127 are computed automatically based on the 3D model. A reference body 50 as describe with respect to FIG. 4 spanning the length of the bone of interest is placed on the affected limb 110. Two or more images are taken of at least one portion of the limb (proximal or distal). A 3D model of the reference portion of the bone (for femoral fractures typically proximal) is established and axes 117 determined. If assistance in reducing the distal portion is desired, the mirrored contra-lateral full bone model (from FIG. 6 and FIG. 7) can be virtually matched in position of the proximal portion of the bone by laying the proximal axes 117, 127 (e.g. proximal shaft axis and neck axis) in a best-fit congruence. Using the reference body 50 to carry the proximal reference into the distal fluoroscopic imaging, the contour and/or axes/landmarks 116/117, 126/127 can be overlaid in the images as shown in FIG. 9. This can be used by the surgeon as reference for reduction. The contra-lateral (target) contour can be displayed on any subsequent image if desired. Adjustment of the overlay could include accepting or dialing in shortening or angle deviations. For more detailed comparison and information on the achieved quality of reduction, the surgeon can choose to also take 2 or images of the distal portion of the bone. This way, also for the broken bone a 3 D model as in FIG. 7 can be established and the system can indicate things as Anteversion angle, Varus angle and bone length which can then be compared directly to equivalent values for the contralateral side or to anatomical averages e.g. from the literature. Being able to provide reduction assist mainly in length/rotation/alignment is a huge medical benefit, especially considering that this can be achieved without pre-operative CT or even pre-operative full-length x-ray or radio images.

Beside the reduction of the long bone, overlaying the contour of the mirrored contra-lateral bone can also be useful in aiding intra-articular reduction, may it be for simple fracture patterns as show in FIG. 10 or more complex fracture patterns. In this use case, the mirrored CI-model 125, 147 could be brought into congruence with the largest/reference fragment 131, either manually or automatically. With image/contour overlays in subsequent images the reduction of the fragments could be facilitated. While all previous descriptions are not reliant on pre-operative 3D-imaging (CT), CT imaging data could be taken advantage of in highly related techniques. Segmented CT of unaffected limb could be used as an alternative to establishing a 3D model, re-alignment steps as described above. Landmark/axes detection could be performed used same method as in the fluoroscopy-based technique. The segmented CT scan of the fractured bone could be virtually reduced (Puzzle) using best fit shape matching either to the contra-lateral side or thorough shape modelling by comparison with a virtual bone database. With the segmented CT-scan of the fractured bone in the background, the system could identify the position and pose of individual fragments using one or more images, as describe with respect to FIG. 1 and FIG. 2. The reference body mentioned above would again enable here to unite multiple views for an accurate spatial position/pose identification. This can then again be compared by image overlay or numerical values to the target coming other from contralateral side or from virtual reduction.

Figure 12:
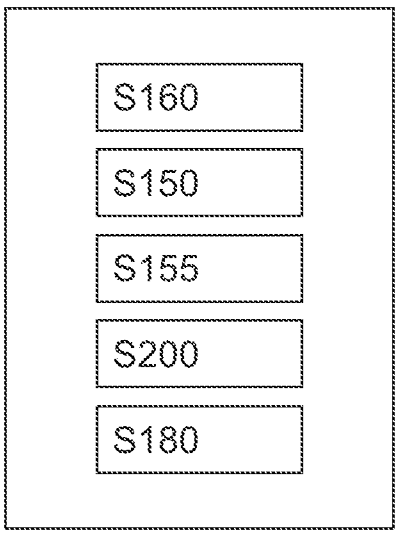
FIG. 12: illustrates a method according to an exemplary embodiment.

FIG. 12 illustrates a method according to an exemplary embodiment. The method comprises: imaging S160 a plurality of bone fragments 131, 132*a*, 132*b*, 132*c*, 132*d* of a traumatized bone 135 of an affected limb 130, identifying S150 based on said imaging a contour, position and orientation of each of the plurality of the bone fragments 131, 132*a*, 132*b*, 132*c*, 132*d* of the traumatized bone 135 of the affected limb 130, identifying S155 based on at least one of the plurality of identified bone fragments 131, 132*a*, 132*b*, 132*c*, 132*d* a corresponding un-traumatized bone in a bone data base of three-dimensional bone models, allocating S200 the plurality of identified bone fragments 131, 132*a*, 132*b*, 132*c*, 132*d* to corresponding contours and positions of the identified un-traumatized bone of the bone data base of three-dimensional bone models, and visualizing S180 the contour, position and orientation of each of the plurality of the bone fragments 131, 132*a*, 132*b*, 132*c*, 132*d* allocated to a corresponding contour, position and orientation of the identified un-traumatized bone of the bone data base of three-dimensional bone models, so that a re-composed position and orientation of each of the plurality of the bone fragments 131, 132*a*, 132*b*, 132*c*, 132*d* of the traumatized bone 135 of the affected limb 130 in a pre-traumatized state are recognizable.

Figure 13:
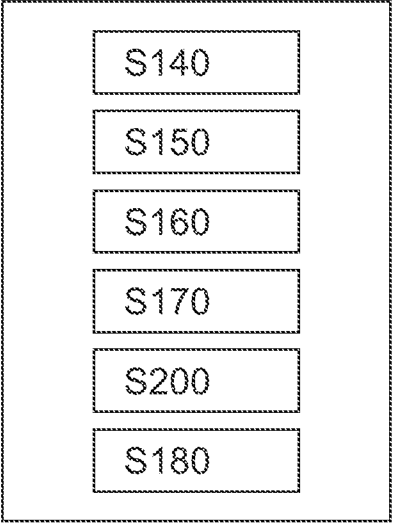
FIG. 13: illustrates a method according to a further exemplary embodiment.

FIG. 13 illustrates a method according to a further exemplary embodiment. This embodiment of the method comprises imaging S140 a bone 145 of an unaffected contra-lateral limb 140, identifying S150 based on said imaging a contour, position and orientation of the bone 145 of the unaffected contra-lateral limb 140, imaging S160 a plurality of bone fragments 131, 132*a*, 132*b*, 132*c*, 132*d* of a traumatized bone 135 of an affected limb 130, identifying S170 based on said imaging of a plurality of bone fragments 131, 132*a*, 132*b*, 132*c*, 132*d* a contour, position and orientation of each of the plurality of the bone fragments 131, 132*a*, 132*b*, 132*c*, 132*d* of the traumatized bone 135 of the affected limb 130, allocating S200 the plurality of identified bone fragments 131, 132*a*, 132*b*, 132*c*, 132*d* to corresponding contours and positions of the identified contour, position and orientation of the bone 145 of the unaffected contra-lateral limb 140, and visualizing S180 the contour, position and orientation of each of the plurality of the bone fragments 131, 132*a*, 132*b*, 132*c*, 132*d* allocated to a corresponding contour, position and orientation of the identified contour, position and orientation of the bone 145 of the unaffected contra-lateral limb 140, so that a re-composed position and orientation of each of the plurality of the bone fragments 131, 132*a*, 132*b*, 132*c*, 132*d* of the bone 135 of the affected limb 130 in a pre-traumatized state are recognizable.

Figure 14:
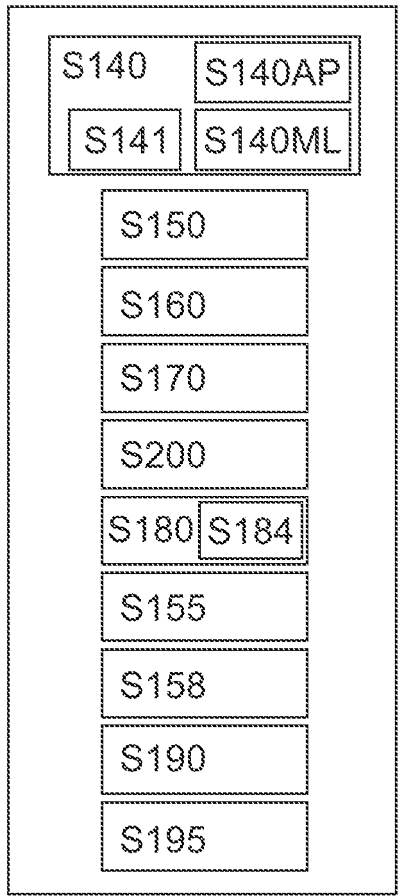
FIG. 14: illustrates a method according to a further exemplary embodiment.
Figure 15:
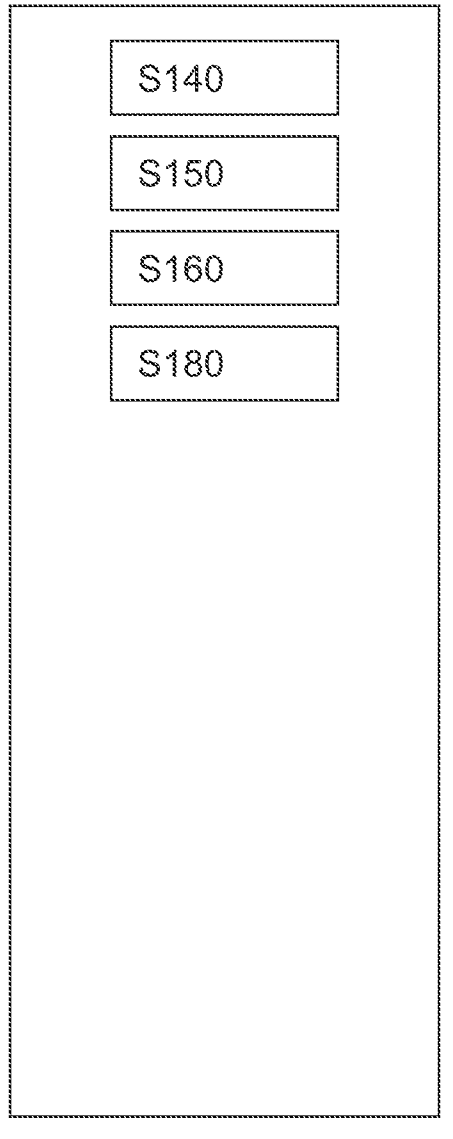
FIG. 15: illustrates a method according to a further exemplary embodiment.

FIG. 14 illustrates method according to further exemplary embodiments. The process steps may be varied according to need. In addition to what is described with respect to FIGS. 12 and 13, the method may selectively and optionally include in imaging a long bone of an unaffected contra-lateral limb S140 taking image from ML S140ML and taking image from AP S140AP this applies for both, imaging first end of long bone of an unaffected contra-lateral limb S141 and imaging second end of long bone of an unaffected contra-lateral limb S142. Further, the method may include not only identifying properties of long bone of unaffected contra-lateral limb S150, but also identifying corresponding bone in a bone data base 155, which may be based on images of real bones, images generated from artificial intelligence algorithms trained by real images and/or be based on statistical shape models. The method may further include visualizing of identified bone fragments in their pre-re-composed state S158. Further the method may include identifying properties of fragments of (long) bone of affected limb S170. In visualizing properties of long bone of the unaffected limb with a long bone fragments S180 further, establishing congruence of fragment with corresponding end of unaffected long bone S184 may be included. Further, the method may include determining amount of spatial deviation of fragment and end of long bone S190 and outputting instructions to change incongruent fragment with respect to an end of a long bone FIG. 15 illustrates a method according to a further exemplary embodiment, according to which the method comprises imaging S140 a long bone 125 of an unaffected contra-lateral limb 120, identifying S150 based thereon a contour, position and orientation of the long bone 125 of the unaffected contra-lateral limb 120, imaging S160 long bone fragments 111, 112 of a long bone 115 of an affected limb 110, and visualizing S180 the identified contour, position and orientation of the long bone 125 of the unaffected contra-lateral limb 120 together with a visualization of long bone fragments 111, 112 of the long bone 115 of an affected limb 110, so that deviations of positions and orientations of the long bone fragments 111, 112 are recognizable.

Figure 16:
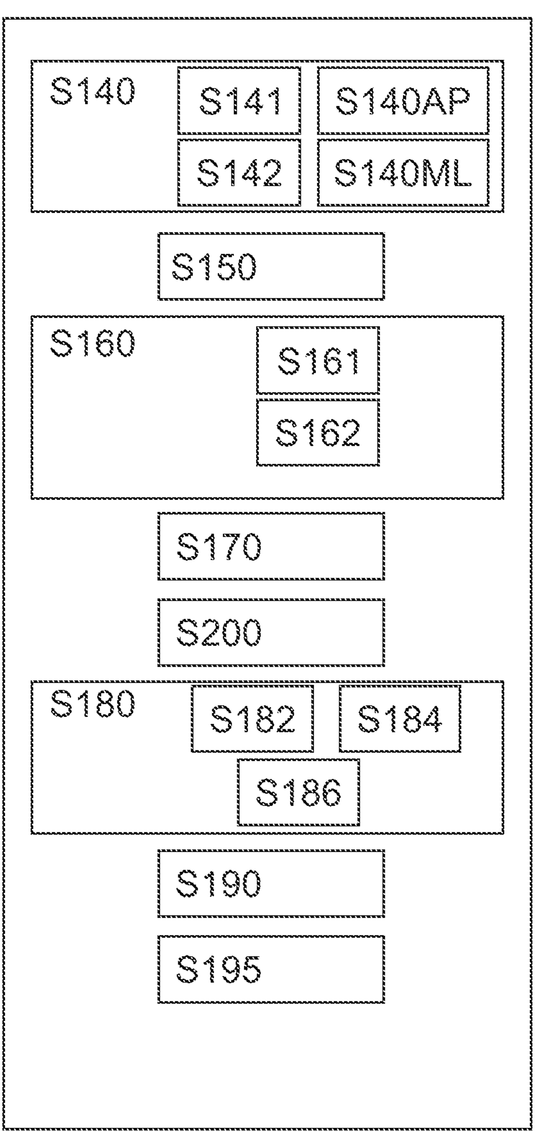
FIG. 16: illustrates a method according to a further exemplary embodiment.

FIG. 16 illustrates a method according to further exemplary embodiments. The process steps may be varied according to need. In addition to what is described with respect to figure FIG. 15, the method may further selectively and optionally include that imaging a long bone of an unaffected contra-lateral limb S140 may include taking image from ML S140ML and taking image from AP S140AP. This may apply to imaging first end of long bone of an unaffected contra-lateral limb S141 and imaging second end of long bone of an unaffected contra-lateral limb S142. Imaging long bone fragments of a long bone of an affected limb S160 may further include imaging first fragment of long bone of affected limb S161 and imaging second fragment of long bone of affected limb S162. Further, the method may include identifying properties of fragments of (long) bone of affected limb S170. Visualizing properties of long bone of the unaffected limb with a long bone fragments S180 may further include visualizing landmarks and axes of visualized long bones S182, establishing congruence of fragment with corresponding end of unaffected long bone S184 and visualizing deviation of incongruent fragment and corresponding end of long bone S186. The method may further include S190 determining amount of spatial deviation of fragment and end of long bone outputting instructions to change incongruent fragment with respect to an end of long bone S195.

REFERENCES

20 radio dense geometry of surgical guiding device
24 fiducial markers
50 surgical reference body
51 first leg of surgical reference body
52 second leg of surgical reference body
60 radio dense geometry of surgical reference body
61 first radio dense sub-geometry of surgical reference body
62 second radio dense sub-geometry of surgical reference body
63 third radio dense sub-geometry of surgical reference body
64 fiducial markers
65 unique radio projection of radio dense geometry of surgical reference body
66 unique radio projection of the first sub-geometry of surgical reference body
67 unique radio projection of the second sub-geometry of surgical reference body
68 unique radio projection of the third sub-geometry of surgical reference body
80 optical pattern
100 patient's anatomy
110 affected limb
111 first long bone fragment of affected limb
112 second long bone fragment of affected limb
115 long bone of affected limb
116 characteristic landmark of long bone of affected limb
117 characteristic axis of long bone of affected limb
120 contra-lateral unaffected limb
121 first end of long bone of unaffected limb
122 second end of long bone of unaffected limb
125 long bone of unaffected limb
126 characteristic landmark of long bone of unaffected limb
127 characteristic axis of long bone of unaffected limb
130 affected limb of bone fragments
131 bone fragment of a bone of an affected limb
132*a-d* bone fragments of a bone of an affected limb
135 traumatized bone of an affected limb
136 characteristic landmark of traumatized bone
137 characteristic axis of traumatized bone
140 contra-lateral unaffected limb of bone fragments
145 bone of an unaffected limb
146 characteristic landmark of bone of contra-lateral unaffected side
147 characteristic axis of bone of contra-lateral unaffected side
S140 imaging a long bone of an unaffected contra-lateral limb
S140ML taking image from ML
S140AP taking image from AP
S141 imaging first end of long bone of an unaffected contra-lateral limb
S142 imaging second end of long bone of an unaffected contra-lateral limb
S150 identifying properties of long bone of unaffected contra-lateral limb
S155 identifying corresponding bone in a bone data base
S158 visualizing of identified bone fragments in their pre-re-composed state
S160 imaging long bone fragments of a long bone of an affected limb
S161 imaging first fragment of long bone of affected limb
S162 imaging second fragment of long bone of affected limb
S170 identifying properties of fragments of (long) bone of affected limb
S175 identifying long bone fragments in a bone data base
S180 visualizing properties of long bone of the unaffected limb with a long bone fragments
S182 visualizing landmarks and axes of visualized long bones
S184 establishing congruence of fragment with corresponding end of unaffected long bone
S186 visualizing deviation of incongruent fragment and corresponding end of long bone
S190 determining amount of spatial deviation of fragment and end of long bone
S195 outputting instructions to change incongruent fragment wrt end of long bone
S200 allocating bone fragments to corresponding identified bone of the bone data base
ML first side, first view, medio lateral side/view
AP second side, second view, anterior posterior side/view

The invention claimed is:

1. A method for reproducing a position and orientation of bone fragments of a traumatized bone of an affected limb, the method comprising:

receiving imaging of a plurality of bone fragments of the traumatized bone of the affected limb, identifying based on said imaging a contour, position and orientation of each of the plurality of the bone fragments of the traumatized bone of the affected limb, identifying based on at least one of the plurality of identified bone fragments a corresponding un-traumatized bone in a bone data base of three-dimensional bone models, allocating the plurality of identified bone fragments to corresponding contours and positions of the identified un-traumatized bone of the bone data base of three-dimensional bone models, and visualizing the contour, position and orientation of each of the plurality of the bone fragments allocated to the corresponding contour, position and orientation of the identified un-traumatized bone of the bone data base of three-dimensional bone models, so that a re-composed position and orientation of each of the plurality of the bone fragments of the traumatized bone of the affected limb in a pre-traumatized state are recognizable.

2. The method of claim 1, wherein allocating the plurality of identified bone fragments to corresponding contours and positions of the identified bone of the bone data base of three-dimensional bone models, comprises a best fit contour algorithm with iterative closest point algorithm.

3. The method of claim 1, wherein allocating the plurality of identified bone fragments to corresponding contours and positions of the identified bone of the bone data base of three-dimensional bone models comprises a best fit algorithm based on an identification of characteristic anatomical landmarks and/or characteristic axes and bringing the characteristic anatomical landmarks and/or the characteristic axes into congruence.

4. The method of claim 1, wherein visualizing the contour, position and orientation of each of the plurality of the bone fragments allocated to the corresponding contour, position and orientation of the identified contour, position and orientation of the bone of the unaffected contra-lateral limb or of the bone data base includes allocating each of the plurality of the bone fragments a different color.

5. The method of claim 4, further comprising outputting instructions to a user on how to change a position and orientation of the incongruent bone fragments so as to arrive at a more visualized congruence of the incongruent bone fragments with the corresponding bone of at least one of the unaffected limb or the bone data base.

6. The method of claim 4, further comprising at least one of:

visualizing the contour, position and orientation of each of the plurality of the bone fragments allocated to the corresponding contour, position and orientation of the corresponding bone of at least one of the unaffected limb or the bone data base;

determining an amount of spatial deviation of the visualized incongruent bone fragments from the corresponding contour, position and orientation of the corresponding bone of at least one of the unaffected limb or the bone data base; or outputting instructions to a user on how to change a position and orientation of the incongruent bone fragments so as to arrive at a more visualized congruence of the incongruent bone fragments with the corresponding bone of the unaffected limb or from the bone data base, respectively, is repeated until a predetermined amount of visualized congruence of the incongruent bone fragments with the corresponding bone of the unaffected limb or from the bone data base, respectively, is achieved.

7. The method of claim 1, further comprising visualizing a contour, position and orientation of each of the plurality of the identified bone fragments of the bone of the affected limb in their pre-re-composed state, wherein visualizing a contour, position and orientation of each of the plurality of the identified bone fragments of the traumatized bone of the affected limb in their pre-re-composed state includes visualizing each of the plurality of the bone fragments in a different color corresponding to an allocated color of the plurality of re-composed bone fragments.

8. The method of claim 1, wherein visualizing the identified contour, position and orientation of the bone fragments includes visualizing of characteristic landmarks and/or characteristic axes of the respective visualized bone fragments and bones.

9. The method of claim 1, wherein visualizing the identified contour, position and orientation of the plurality of bone fragments includes establishing a congruence of one of the bone fragments with a corresponding contour, position and orientation of the corresponding bone of at least one of an unaffected limb or the bone data base, and visualizing a spatial deviation of incongruent other ones of the bone fragments.

10. The method of claim 9, further comprising determining an amount of spatial deviation of the visualized incongruent bone fragments from the corresponding contour, position and orientation of the corresponding of at least one of the unaffected limb or the bone data base.

11. A method for reproducing a position and orientation of bone fragments of a traumatized bone of an affected limb, the method comprising:

receiving imaging of a bone of an unaffected contra-lateral limb, identifying based on said imaging a contour, position and orientation of the bone of the unaffected contra-lateral limb, receiving imaging of a plurality of bone fragments of the traumatized bone of the affected limb, identifying based on said imaging of the plurality of bone fragments a contour, position and orientation of each of the plurality of the bone fragments of the traumatized bone of the affected limb, allocating the plurality of identified bone fragments to corresponding contours and positions of the identified contour, position and orientation of the bone of the unaffected contra-lateral limb, and visualizing the contour, position and orientation of each of the plurality of the bone fragments allocated to the corresponding contour, position and orientation of the identified contour, position and orientation of the bone of the unaffected contra-lateral limb, so that a re-composed position and orientation of each of the plurality of the bone fragments of the bone of the affected limb in a pre-traumatized state are recognizable.

12. The method of claim 11, further comprising:

confirming allocation by identifying based on at least one of the plurality of identified bone fragments the corresponding un-traumatized bone in a bone data base of three-dimensional bone models, and comparing the visualized contour, position and orientation of each of the plurality of the bone fragments allocated to the corresponding contour, position and orientation of the identified contour, position and orientation of the bone of the unaffected contra-lateral limb with the corresponding un-traumatized bone of the bone data base of three-dimensional bone models.

13. A method for reproducing a position and orientation of long bone fragments of a long bone of an affected limb, the method comprising:

receiving imaging of a long bone of an unaffected contra-lateral limb, identifying based thereon a contour, position and orientation of the long bone of the unaffected contra-lateral limb, receiving imaging of the long bone fragments of the long bone of the affected limb, visualizing the identified contour, position and orientation of the long bone of the unaffected contra-lateral limb together with a visualization of long bone fragments of the long bone of an affected limb, so that deviations of positions and orientations of the long bone fragments are recognizable.

14. The method of claim 13, wherein receiving imaging of the long bone of the unaffected contra-lateral limb includes receiving imaging of a first end of the long bone of the unaffected contra-lateral limb and separately receiving imaging of a second end of the long bone of the unaffected contra-lateral limb.

15. The method of claim 13, wherein receiving imaging of the long bone of the unaffected contra-lateral limb includes receiving imaging of the long bone of the unaffected contra-lateral limb having attached thereto a surgical reference body with a radio dense geometry having a unique radio projection for each orientation of the surgical reference body, and representing an unambiguous position and orientation of the long bone of the unaffected contra-lateral limb.

16. The method of claim 13, wherein identifying a contour, position and orientation of the long bone of the unaffected contra-lateral limb comprises identifying a corresponding long bone in a bone data base of three-dimensional long-bone models including at least one of a contour, a position or an orientation of the corresponding long bone.

17. The method of claim 13, further comprising identifying a contour, position and orientation of the long bone fragments of the affected limb and identifying based thereon long bone fragments in a bone data base of three-dimensional long bone models including a contour, position and orientation of a corresponding long bone.

18. The method of claim 13, wherein visualizing the identified contour, position and orientation of the long bone of the unaffected contra-lateral limb together with a visualization of long bone fragments of the long bone of the affected limb includes visualizing of at least one of characteristic landmarks or characteristic axes of the respective visualized long bones.

19. The method of claim 13, wherein visualizing the identified contour, position and orientation of the long bone of the unaffected contra-lateral limb together with a visualization of long bone fragments of a long bone of an affected limb includes establishing a congruence of one of a first long bone fragment and a second long bone fragment of the long bone of the affected limb with a corresponding one of a first end and a second end of the long bone of the unaffected limb, and visualizing a deviation of the incongruent other one of the first fragment and the second fragment of the long bone of the affected limb from the corresponding one of the first and second ends of the long bone of the unaffected limb.

20. The method of claim 13, wherein visualizing the identified contour, position and orientation of the long bone of the unaffected contra-lateral limb together with a visualization of long bone fragments of the long bone of the affected limb includes establishing a congruence of one of a first long bone fragment and a second long bone fragment of the long bone of the affected limb with a corresponding one of a first end and a second end of a long bone of a data base of three-dimensional bone models, and visualizing a deviation of the incongruent other one of the first fragment and the second fragment of the long bone of the affected limb from the corresponding one of the first and second ends of the long bone of the data base of three-dimensional bone models.

* * * * *